United States Patent
Yang

[11] Patent Number: 5,868,149
[45] Date of Patent: Feb. 9, 1999

[54] RETRACTABLE TOOTHPICK

[76] Inventor: Ching-Jiun Yang, 2F., No.4., Alley 1, Lane 564, Hsin Fu Rd., Hsinchuang, Taipei, Taiwan

[21] Appl. No.: 946,381

[22] Filed: Oct. 7, 1997

[51] Int. Cl.⁶ ...................................................... A61C 15/00
[52] U.S. Cl. .......................... 132/328; 132/329; 433/141
[58] Field of Search ..................................... 132/321, 328, 132/329; 433/141; 606/181, 185

[56] References Cited

U.S. PATENT DOCUMENTS

| | | | |
|---|---|---|---|
| 97,391 | 11/1869 | Graham et al. | 132/328 |
| 209,566 | 11/1878 | Holland | 132/328 |
| 237,093 | 2/1881 | Crowell | 132/328 |
| 1,679,651 | 8/1928 | Crowell | 132/328 |
| 2,510,194 | 6/1950 | Thomas | 132/328 |
| 4,509,541 | 4/1985 | Manciocchi, Jr. | 132/328 |
| 5,046,212 | 9/1991 | O'Conke | 132/328 |
| 5,318,581 | 6/1994 | Sunmo | 606/181 |

*Primary Examiner*—Ralph A. Lewis
*Attorney, Agent, or Firm*—Bacon & Thomas

[57] ABSTRACT

This invention named "the expanding bi-toothpick with dual controls for pushing and extracting" is mainly composed of the outer rod which is a thin rod designed to extract the food remains in the tooth gap directly and the inner stick which is a thin stick and can go deep into the tooth gap to clean the dregs directly. Besides there is a elastic device between these parts to provide the user dual controls for selecting pushing or picking the stick's end to reach the purpose of cleaning the teeth or the tooth gaps.

3 Claims, 7 Drawing Sheets

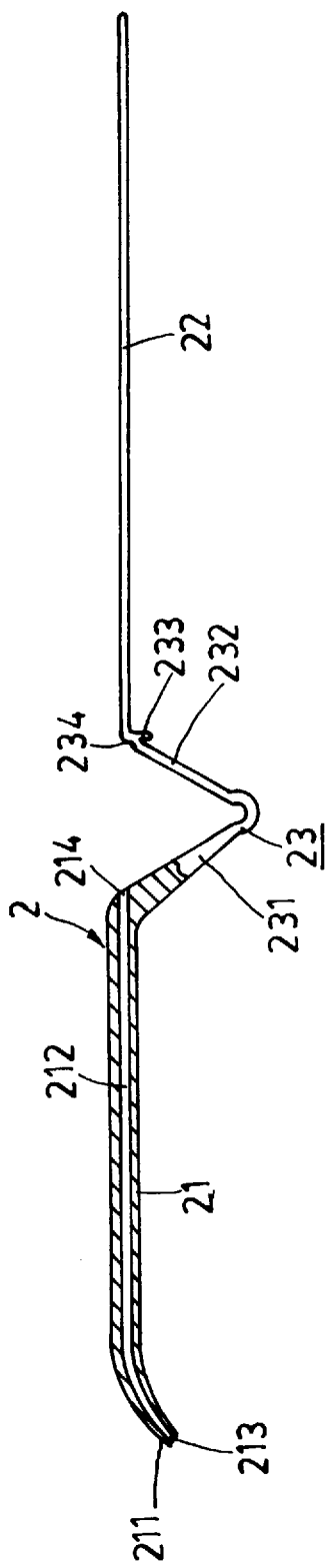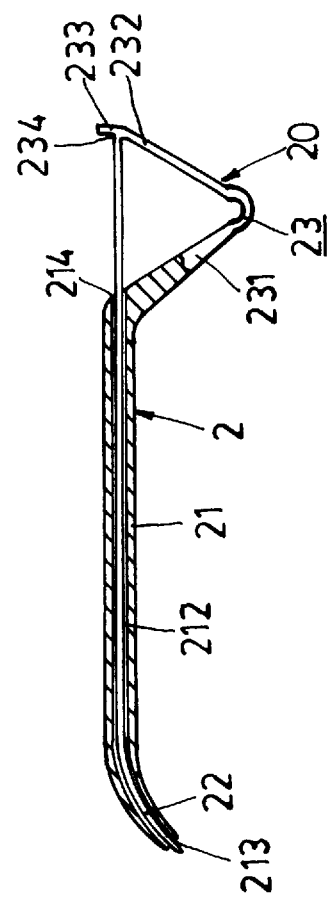

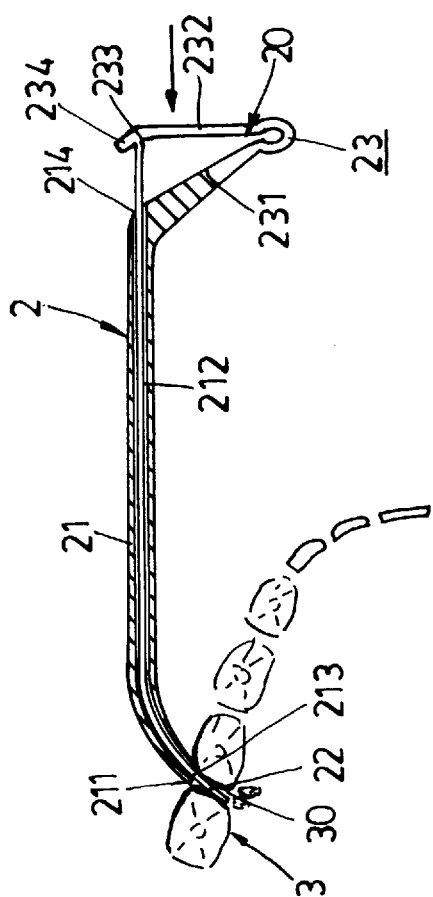
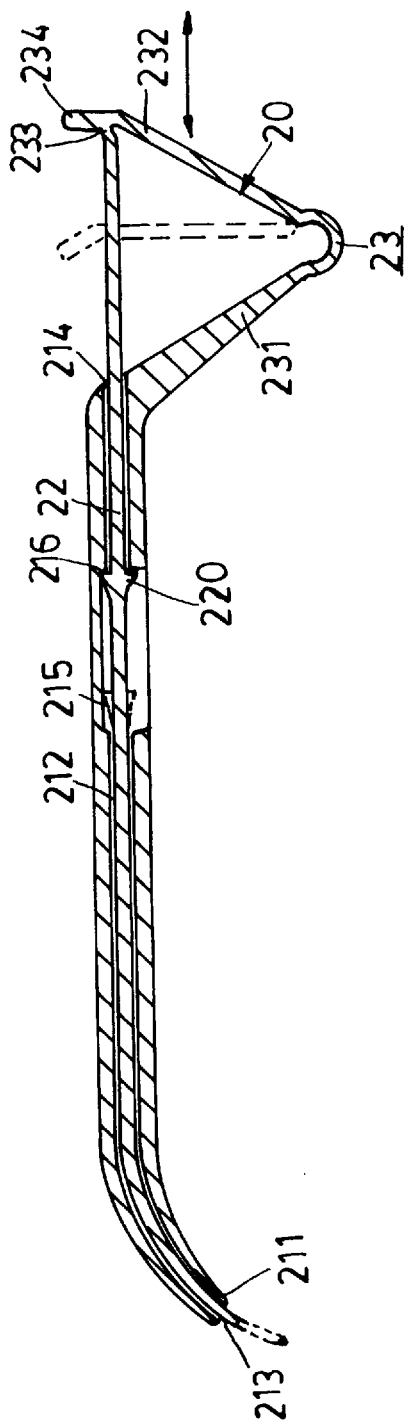
Fig. 11
Fig. 12

RETRACTABLE TOOTHPICK

BACKGROUND

The traditional toothpick with a 2 mm diameter section is usually made of plastic as in FIG. 1 or of wood as in FIG. 2. One or both ends of the toothpick are pointed by gradually narrowing the diameter of the tip. The method of extracting food remains from the gaps between the teeth, using this kind of the toothpick, is to insert the toothpick in the gaps directly. This can result in the gap becoming wider because the deeper the toothpick is inserted into the gap, the wider the section of the toothpick would become when the toothpick is used for a period of time. Also the traditional toothpick can not be inserted into a narrow gap near the tooth surface due to different gap shape of everyone. If the tough food remains is picked out by force from the narrow gap, the gap would become wider, the pointed end of the toothpick might be broken and left in the gap, and the teeth or gum might also be injured.

Because the traditional toothpick has the said defects, the floss on a stick as in FIG. 3 was developed for improvement. It is made by a formed rod which has a proper length of a bow with floss tightened on both sides of the bow. However, it is not easy to use the formed rod when putting the floss into the tooth gap. Especially since the user would display unrefined manners by having to open his/her mouth wide to insert the rod. Besides, only the outside incisor can be cleaned by this kind of toothpick, as it is not convenient for cleaning the cheek teeth of the mouth due to the wrong inserting direction to put the floss into the tooth gap. It is furthermore difficult for the users without any tooth gap near the surface of teeth.

The following venders aiming at improving the said defects of the traditional toothpick are continuously developing new devices. For example as in FIG. 4 to form the end of the toothpick into a sheet, or as in FIG. 5 to connect any special device like a brush or a little salience on one side of the toothpick to clean the food remains better or to have the massage function. However, most of the said toothpick with a single rod grip only can pick the outside teeth easily, but not for the inner cheek teeth. If you wanted to extract the food remains from the inner cheek teeth, the toothpick would have to be held upside down, and the holding angle would not be easy to control. Furthermore, it is very ill mannered and also not healthy for the user to have to open his mouth widely to provide space for the toothpick Meanwhile the mouth or tongue could be also pricked by a too long toothpick. Therefore a kind of hook on the toothpick was developed as in FIG. 6. It is made by a bending rod with an adjustable angle function at the end of a toothpick and is able to clean the inner cheek teeth. But the angle between the straight rod and the bending hook could be very big that the toothpick need sufficient space to act. This means the user still has to open his mouth widely to provide enough space for controlling the toothpick. The pointed end of the hook is also the same as a normal toothpick's pointed end which is stretched from reducing gradually the section of the rod. The defects that make the user's tooth gap wider still exist. We can say that this kind of toothpick still can not improve the traditional structure effectively.

SUMMARY OF THE INVENTION

This invention is a type of bi-toothpick with dual axial operating function for extracting food remains from tooth gaps and can be operated in an up and down motion and also go deep into the tooth gap to push the food remains horizontally away from the tooth. It consists of an inner rod and an outer a tube. The inner rod which is flexible and able to be stretched out can be set up in the hollow of the outer tube as a guide. The user can extract the food remains from the tooth gap by pushing the inner rod to the end of the outer tube and let the inner rod stretch out to a proper length and push the food remains directly outwards. The user does not have to use force to pick upwards which might cause enlargement of the tooth gap. It is very convenient for the user to use this bi-toothpick since it can be operated from the outside surface tooth. The outer tube can also be a toothpick to clean the outside teeth. Therefore the invention can be said to be a type of toothpick with dual manual controls for a pushing or extracting device.

BRIEF DESCRIPTION OF THE DRAWINGS

FIG. 7 is a side view of a first embodiment of the invention.

FIG. 8 is an assembly drawing of FIG. 7 with section view.

FIG. 11 is a section view to show how to use the stretching inner rod of the toothpick to clean the teeth.

FIG. 12 is a section view showing the operation of the first embodiment.

DETAILED DESCRIPTION OF THE PREFERRED EMBODIMENT

Figure 1:
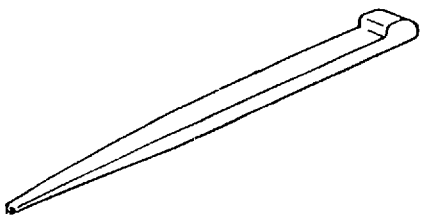
FIG. 1 is an outline drawing of a plastic toothpick.
Figure 2:
FIG. 2 is an outline drawing of a traditional wooden toothpick.
Figure 3:
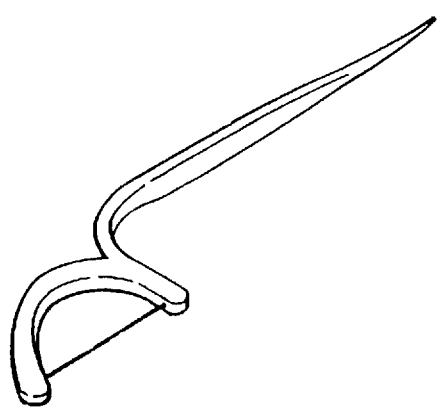
FIG. 3 is an outline drawing of a traditional floss rod.
Figure 4:
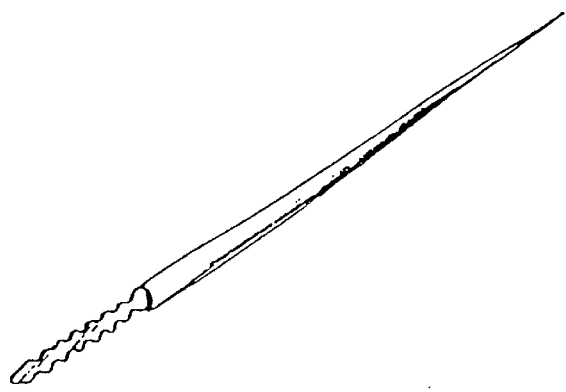
FIG. 4 is an outline drawing of a familiar toothpick with flat tip.
Figure 5:
FIG. 5 is an outline drawing of a familiar toothpick with brush tip.
Figure 6:
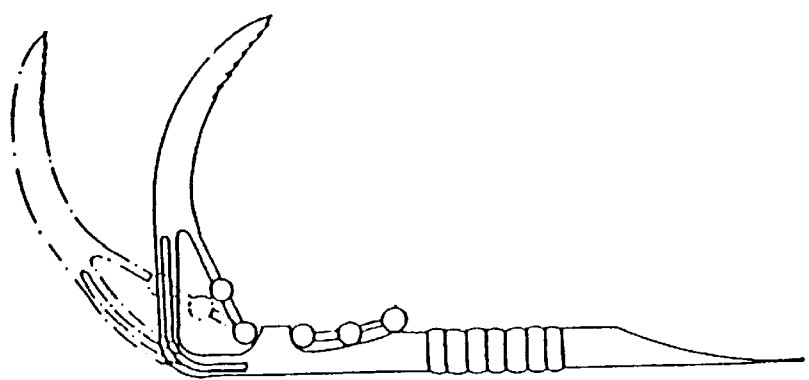
FIG. 6 is an outline drawing of a familiar toothpick with bending hook.
Figure 9:
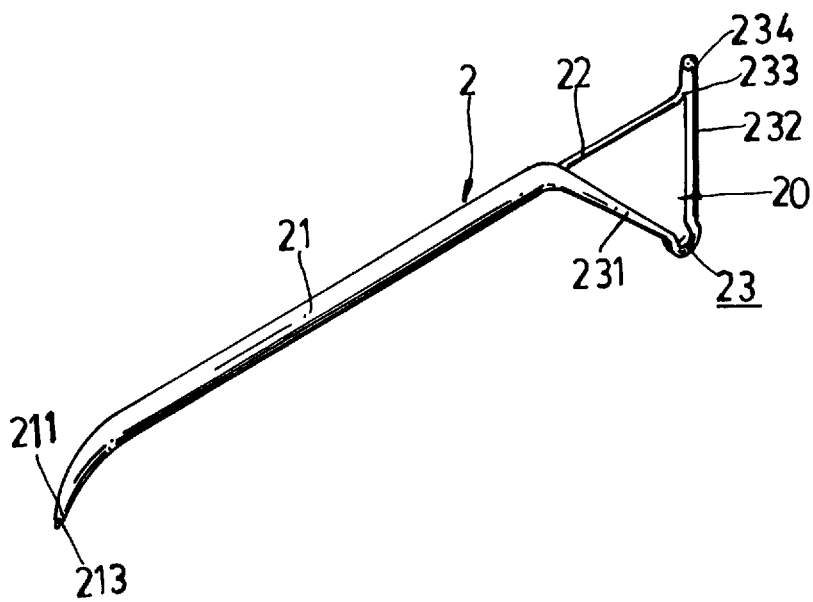
FIG. 9 is a 3D assembly drawing of FIG. 7.

The product shown in FIG. 7 is composed of 3 plastic parts: part A (marked 21) and part B (marked 22) both look like a small rod, the diameter of part B (called "inner rod" below) is smaller than part A (called "outer tube" below ) so that the "inner rod" fits exactly in the inner hole of "the outer tube", part C (marked 23) is a resilient arc linkage placed between 21 and 22, the outer function of this part C is to provide enough elasticity to control the movement of "the inner rod".

The diameter of the outer tube front end is decreased gradually to form an tapered end 211, and we drilled a hole through the outer tube from 213 to 214 (refer to FIG. 7) to form a pipe, and this pipe hole is prepared for the "inner rod".

As shown in FIG. 7, the other end of the "inner rod" links with the resilient arc linkage 23, which is composed of 2 arms 231 and 232, the arm 232 and arm 231 links with the inner rod 22 and the outer tube 21 separately. The other purpose of arc linkage 23 is to construct an "elastic area" (marked 20 in the figure), so that the user could just easily press and release arm 232 to make the inner rod move forward and backward along the pipe hole inner of the outer tube.

Furthermore, there is a small thin bar (which is marked 234 in the figure) placed between arm 232 and rod 22 in order to provide enough curvature for the assembly of the inner rod and the outer tube.

We abbreviate this invention "Bi-toothpick". To assemble the "Bi-toothpick" by turning the inner rod" around and then inserting into the hole of the outer tube. We should let the front tip of the rod jut out from the mouth of the outer tube 213, so that 1) the user can use the rod's front tip to aim at any crevice of the teeth, 2) the user can also press the arm 232 to easily control the position of the rod's front tip, 3) the user could press the arm 232 to make the rod's front tip move forward to clean the dregs in the crevice, and if the user release the arm 232 then the elastic area 20 provide enough elasticity to force both the arm 232 and the rod's tip to move backward.(refer to FIG. 8,9)

Figure 10:
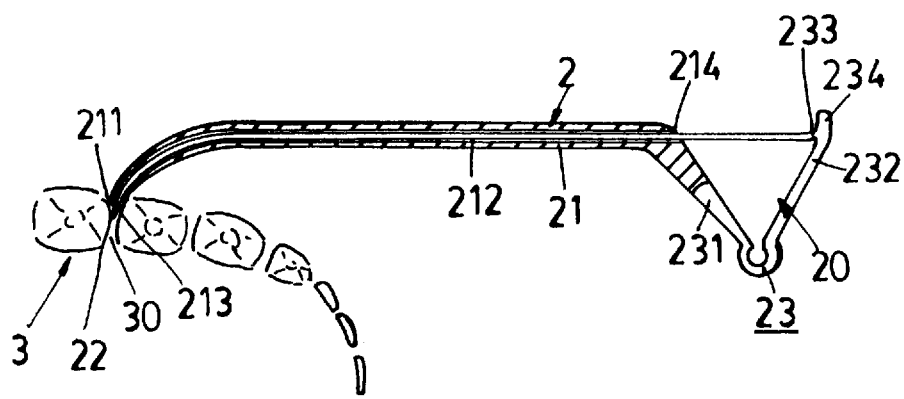
FIG. 10 is a section view to show how to use the outer tube of the toothpick to clean the teeth.

FIG. 10 demonstrates how to use this toothpick. Users can put the mouth of the outer tube 211 against the rim of teeth, and then press arm 232 to make the rod's end enter the crevice of teeth and clean the dregs. The user could easily enjoy the operation of the bi-toothpick and clean the dregs rapidly, to the contrary where users must always adjust the position and direction of toothpicks when they use the tranditional type.

FIG. 12 shows an improvement of this invention. There are only two differences between FIG. 12 and FIG. 8: the first are two small shields is added to the inner rod in order to provide support, which could prevent the inner rod from moving too far; the second difference is that a bigger hole is drilled inside the outer tube in order to provide enough space for the movement of the inner rod.

The other purpose of the two small shields is to limit the stroke of the inner rod, so that we can improve the stability of moving the inner rod. Thus, at the same time the user can operate this bi-toothpick easily.

Figure 13:
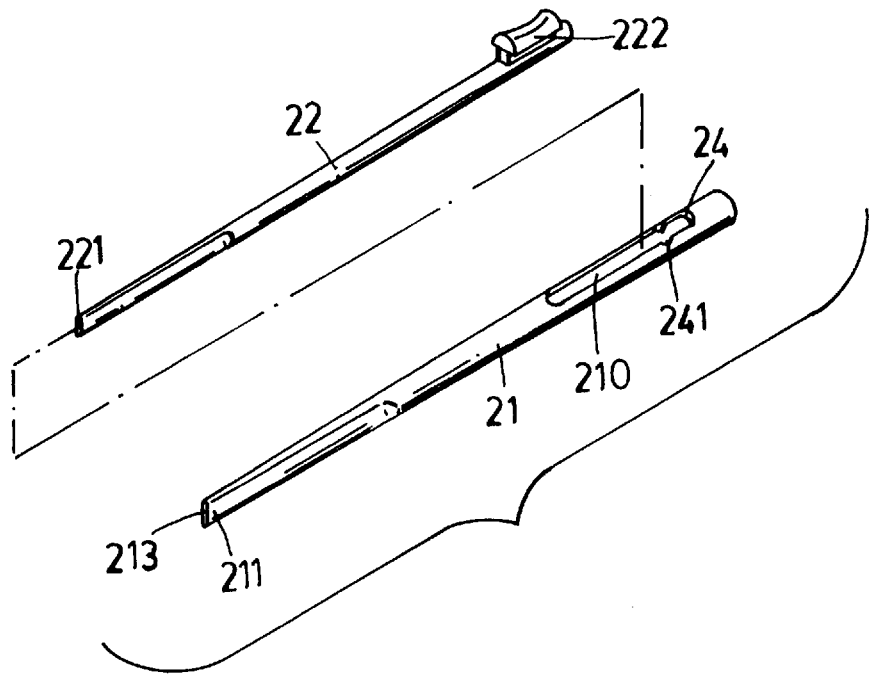
FIG. 13 is an exploded perspective example of the invention.
Figure 14:
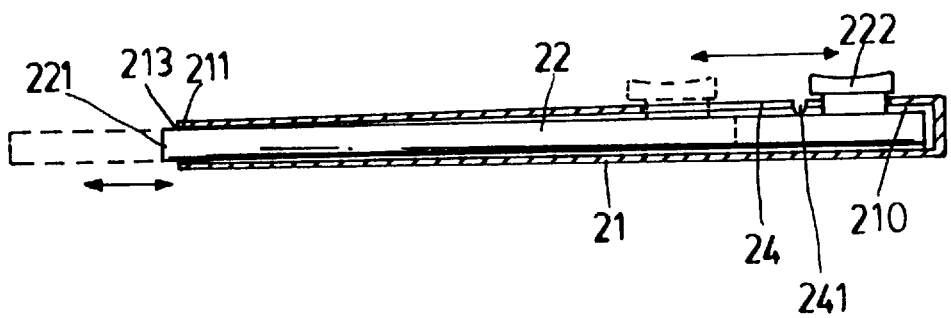
FIG. 14 is a assembly drawing of FIG. 13.

FIG. 13 and FIG. 14 shows another design of this invention. FIG. 13 also shows an outer tube and inner rod, but both the outer tube and inner rod have a more flat tip, furthermore, there is another long hole on the surface of the outer tube, and a button 222 attached to the inner rod (FIG. 14 shows the assembly of this device in detail).

There is a deep cut 241 near the end of the hole, the purpose of this design is to prevent this device device from been recycled. The user can break this bi-toothpick by applying force on the cut after using it.

Once again the user can place the outer tube's front end against any teeth's surface and then push the button on the inner stick to make the rod move forward and backward and to aim at crevices and to clean the dregs, the function of the button on the rod and hole on the outer tube is to limit the stroke of the rod and to ensure the inner rod moves more stable and smoothly.

Figure 15:
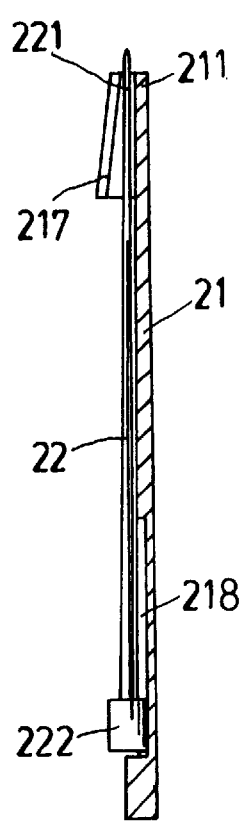
FIG. 15 is a assembly drawing of the 3rd example of the invention.

FIG. 15 is the third improvement of this invention. This time we place the button at the end of the inner rod, and a cavity is drilled on the outer tube, meanwhile we have a cylinder tube on the end of outer tube, so that the user can press the button to make the rod move backward and forward, and to clean the teeth.

Figure 16:
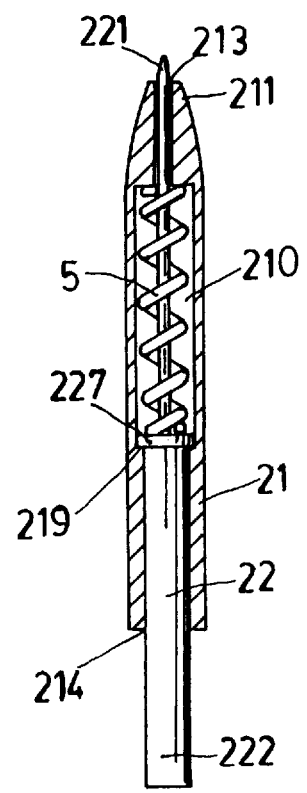
FIG. 16 is a assembly drawing of the 4th example of the invention.

FIG. 16 shows the 4th improvement of this invention. There is a bigger cavity inside the outer tube, and we have a shield placed in the middle of the inner rod, and the space between the shield and cavity is full of some elastic material (spring,etc), so that the user can easily make the inner rod move forward just by pressing the end of the inner rod, and the inner rod will move back automatically when the user releases the end. For the same reason mentioned previously, the user could clean his teeth's dregs thoroughly just by pressing and releasing the rod's end.

We may say that this kind of bi-toothpick is more convenient and easier to use compared with the traditional toothpick.

I claim:

1. A retractable toothpick comprising:

a rod having a front tip and a rear end;

a hollow tube having a front end and a rear end;

a resilient arc linkage connecting said rear end of the rod and said rear end of the tube;

a bar connected to the arc linkage for grasping by a user; and said rod being disposed within said tube for sliding movement therein between an extended position of use and a retracted position of storage in which the front tip of the rod remains outwardly of the front end of the tube, whereupon the rod is disposed in the extended position when pressure is applied to the bar by the user and the resiliency of the arc linkage restores the rod to the retracted position upon release of pressure by the user.

2. The retractable toothpick of claim 1, wherein the front end of the tube is tapered and forms a gradual bend relative to a remainder portion of the tube.

3. The retractable toothpick of claim 1, wherein said rod has a raised portion disposed between the front tip and the rear end of the rod; and the interior of the tube includes an increased diameter portion and the rod includes a shield positioned within the increased diameter portion for engaging a pair of opposite end walls of the increased diameter portion, thereby limiting the degree of extension and retraction of the rod.

* * * * *